United States Patent [19]

Cerf et al.

[11] 4,314,965
[45] Feb. 9, 1982

[54] STERILIZATION PROCESS USING A HEAT EFFECT ADDITIVE

[75] Inventors: Olivier Cerf, Paris; Georges Grenier, Epernon; Jean Hermier, Paris; Alain Rancurel, Leves par Mainvilliers, all of France

[73] Assignee: Laboratoires Pharmascience, France

[21] Appl. No.: 136,512

[22] Filed: Apr. 2, 1980

[30] Foreign Application Priority Data

May 16, 1979 [FR] France ................. 79 12403

[51] Int. Cl.³ .......................... A61L 2/04; A61L 2/18
[52] U.S. Cl. .................................... 422/28; 424/325
[58] Field of Search .............. 422/28, 31; 424/325

[56] References Cited

U.S. PATENT DOCUMENTS 3,511,706  5/1970  Orr ................................ 422/28 X
3,762,874  10/1973  Berry ............................. 422/28
4,196,217  4/1980  Rancurel et al. ............... 424/316

FOREIGN PATENT DOCUMENTS 2163307  7/1972  Fed. Rep. of Germany ........ 422/28
2301235  9/1976  France .

Primary Examiner—Barry Richman
Attorney, Agent, or Firm—Maky, Renner, Otto & Boisselle

[57] ABSTRACT

A process of sterilization or decontamination of apparatus, characterized in that an aqueous solution containing at least 0.01% of a compound of the formula

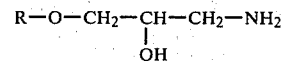

in which R represents a $C_5$–$C_{14}$ n-alkyl radical in the form of the base or a salt thereof, is applied to the apparatus at a temperature in the range of 30° to 120° C. at atmospheric pressure.

The process is suitable in particular for the sterilization of milk processing circulation equipment.

5 Claims, No Drawings

STERILIZATION PROCESS USING A HEAT EFFECT ADDITIVE

FIELD OF THE INVENTION

The present invention relates to a sterilization process using a heat effect additive.

In the field of bacteriological purity of materials, more particularly sterilization, the main problem lies in the destruction of the bacterial spores.

Many bacteria are capable of surviving temperatures very much higher than their normal growth temperature. Although this property is found in heat resistant non-sporulating bacteria. It is mainly a characteristics of bacteria which form endospores.

The endospores survive temperatures which would be lethal to the corresponding vegetative cells. The spores of certain bacilli can be heated to temperatures above 100° C. for several hours without being sterilised. Although the spores are destroyed at a high temperature, their mortality rate is much lower than that of the corresponding vegetative cells.

BACKGROUND OF THE INVENTION

The destruction of bacterial spores occurs in two operations which are very different from each other in their aims:

Sterilization with a view to destruction of all the bacterial spores present with a degree of reliability compatible with the commercial requirements for sale of the sterile product distributed in sterile apparatus. An example of this is the sterilization of various milk processing equipment.

Decontamination of lower the spore count to a level considered to be acceptable for the subsequent use of the product. Such an operation is carried out, for example, in certain areas of the vegetable processing industry. Decontamination may precede sterilization in cases where pieces or sets of pieces are difficult to sterilize in situ.

In the context of the present invention, it should be understood that although the process described below is more particularly intended for sterilization, it is equally or even more applicable to the decontamination of apparatus and materials.

A sterilization treatment uses a sporicidal agent for a given time at a given temperature.

By "sterilization parameters" are meant the combination of time and temperature which characterises a given process and produces a given sterilisation effect.

Calculation of the parameters is based on precise knowledge of the treatment conditions, in particular the pH, temperature and activity of the water, and of the kinetics of destruction of the bacterial spores under these conditions. To make the calculation, the data relating to bacterial spores of the most heat-resistant strains which it is desired to destroy are used. These strains, (or strains with similar properties), should normally be present in the product or on the material to be sterilized and must be capable of developing in the product after sterilization.

The sterilization parameters can only be calculated if the destruction kinetics of the bacterial spores obey a constant law which is reproducible from one treatment to the next. Sterilization by heat has a considerable advantage from this point of view. The destruction kinetics of bacterial spores may generally be represented by the following equation:

$$E = \log(N_o/N) = t/D_t \tag{1}$$

where E, the sterilization effect (defined as the logarithm of the ratio of $N_o$, the initial number of bacterial spores, to N, their number after a destruction treatment of duration t) is the ratio of the treatment time t to a constant $D_T$ characteristic of the treatment and the strain, also known as the decimal reduction at temperature T. The destruction kinetics can therefore easily be represented by a straight line obtained by plotting log N as a function of t.

Unfortunately, many sporicidal treatments exist in which the destruction kinetics do not obey such a simple law. These include in particular treatment with chemical substances, where the kinetics of destruction are represented by a "trail" or scattering of points: "biphasic" kinetics or kinetics characterised by an upward concavity (in both cases on semilogarithmic coordinates as mentioned above). To the extent that the reproducibility of such kinetics from one test to another is poor, it is difficult, if not impossible, to calculate the parameters for a sporicidal treatment which has the serious disadvantage described above.

Numerous examples of destruction kinetics which cannot be described by equation (1) are found in the following publication: "The trail of survival curves of bacterial spores" by O.CERF, Journal of Applied Bacteriology (1977) 42: 1-19.

The cases of treatments with an alkaline medium, or with methylene glycol, glutaraldehyde, hydrogen peroxide, or ethylene oxide may be briefly mentioned here.

It should be clear that the complete study of a sterilizing agent is a very prolonged and costly operation. This partly explains why, in the case of many chemical additives, considerable difficulties were encountered when these studies were conducted with insufficient thoroughness. It is one of the advantages of the process according to the present invention that the studies which have already been carried out on sterilization by moist heat can to a large extent be used again.

The process according to the present invention uses a heat effect additive which makes it possible for the known curves for moist heat sterilization to be used but under more favourable conditions of temperature and pressure.

Although sterilization with moist heat may be regarded as a sterilization process which produces completely satisfactory results, there are nevertheless certain disadvantages in the methods employed.

Sterilization with moist heat implies the use of temperatures above 100° C. It is well known that each degree of temperature above 100° C. involves a high additional cost. It is therefore of particular interest to be able to achieve sterilization at temperatures below 100° C.

Furthermore, sterilization with steam or with hot water under pressure means that the whole apparatus which is to be contaminated by this process must be capable of withstanding the extra pressure. In the majority of cases this means the use of a technology which requires very costly apparatus. It is therefore particularly important to be able to operate under conditions as close as possible to atmospheric pressure. Particularly in processes for the ultra high temperature sterilization of milk, for example, this means that a simple buffer vat may be used instead of an autoclave, and ordinary heat resistant joints may be used instead of pressure resistant joints.

SUMMARY OF THE INVENTION

The present invention therefore relates to a process for the sterilization of decontamination of apparatus, in which an aqueous solution containing at least 0.01% of a compound acting as heat effect additive corresponding to the following formula

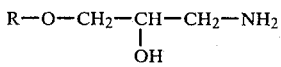

in which R represents a $C_5$ to $C_{14}$ n-alkyl radical, is applied to this apparatus in the form of the base or a salt thereof, at a temperature in the range of 30° to 120° C. at atmospheric pressure, preferably at a temperature from 60° to 100° C., more particularly from 70° to 90° C., for 1 to 60 minutes, in particular from 10 to 30 minutes.

The compounds according to the present invention used as sterilizing agents behave as a heat effect catalyst. As far as the Applicants are aware, this is the first time that such a type of action has been disclosed. In other words, the characteristics of the sporicidal action of moist heat are maintained within a certain interval of temperature, with the exception of the temperature coefficient, which changes from about 10° C. for moist heat to 21.5° C. for a 1% solution of a compound of the following formula:

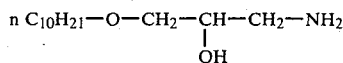

The catalytic effect is shown by a considerable reduction in the absolute value of resistance of the spores. This means that the calculation methods which are well known for sterilization by heat may be used as a whole for the sterilization with these compounds within the temperature range of about 60° to 100° C. at atmospheric pressure.

DETAILED DESCRIPTION

Studies which have been carried out on the process show that to obtain satisfactory sterilization, the apparatus should be kept in contact with a 0.5 to 2% solution of the compound, preferably a 1% solution, for a time in the range of 10 to 30 minutes, preferably about 20 minutes, at a temperature from 70° to 90° C., preferably at a temperature of 80° C.

Among the compounds which are particularly active as heat effect catalyst may be mentioned the compound of the following formula

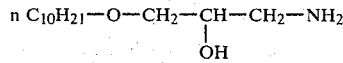

in the form of its hydrochloride, which will hereinafter be referred to as compound A.

The various compounds and the process for preparing them have already been described in French Pat. No. 75 05647 in the name of Laboratoires Pharmascience.

It should be noted that in addition to their property of acting as heat effect catalysts, the compounds according to the invention have numerous other surprising properties which are particularly useful for carrying out the process according to the invention, particularly their non-toxicity, the absence of any irritant effect on the skin and mucous membranes and their very slight corrosive effect on metals and plastics.

The following Examples serve to illustrate how the process according to the present invention may be carried out in practice.

EXAMPLE 1

The sporicidal activity is presented in the form of survival curves, that is to say a graph in which the logarithm of concentration of surviving spores is plotted as a function of time. The survival curve obtained in this manner includes a straight line which may or may not be preceded by a shoulder. This straight portion is characterised by a time of decimal reduction, that is to say the time required to reduce the number of living spores by 90%, symbolised by the letter D.

D is the time required for the survival curve to pass through one logarithmic unit. The value D is expressed in minutes.

Those portions of the survival curves which are straight lines are described by the inverse of their slope, as follows:

$$D = t/(\log N_o - \log N)$$

where t = treatment time of spores in minutes
$N_o$ = number of living spores per milliliter at zero time
N = number of surviving spores per milliliter at time t.

The values for D increase as a function of the resistance of the spores. A latency period and a trail have been observed in some of the survival curves.

A latency period is that part of the survival curve which appears as the shoulder.

A trail is characterised by the slowing down of the decimal reduction time, starting from a certain number of decimal reductions (3 to 4).

(a) General characteristics of the action of compound A

The sporicidal action of compound A in combination with heat has been verified on the spores of Bacillus subtilis var. niger, which is the strain used for reference in the case of chemical sterilization. The following results are obtained:

Compound A at 3% had no action at room temperature (temperature below 30° C.);
at 65° C., addition of compound A considerably reduced the value of D (at pH 7.0: D=2.5 min instead of $6.10^3$ min);
the activity of compound A at 65° C. was optimal at pH 7-8 and minimal at pH 4.5:
the effect of compound A was at a maximum at concentrations at least equal to 0.9% and dissappeared at concentrations below 0.01%.

(b) Choice of a strain for studying the activity of compound A

The resistance of spores of B. subtilis var. niger to compound A was too weak for a precise study for be made within a wide range of temperatures and heating times. Other reference strains available in the laboratory were therefore investigated to find out whether at least one of them would offer sufficient resistance for such a study. After examining about 10 strains, a strain of *B. licheniformis* deposited at the INSTITUT PASTEUR under the number CNCM 1.079 and used in the laboratory for its resistance to hydrogen peroxide was chosen.

The D value at 65° C. in the presence of compound A was 20 minutes at pH 7.0 ($2.10^4$ min in the absence of compound A). The effect of pH and concentration of the solution of compound A was identical to that observed in spores of *B. subtilis* var. *niger*.

(c) Characteristics of the activity of compound A on spores of *B. licheniformis*

Influence of temperature

Within the temperature range of 40° to 80° C., the logarithm of D decreased linearly with temperature. The general characteristics of the action of heat on bacterial spores were thus found again. However, the value for z in the presence of compound A was distinctly higher than in the absence of compound A (21.5° C. instead of 8.9° C. at pH 7.0).

z is the number of degrees Centigrade required for the T.D.T. curve (influence of temperature on the decimal reduction time) to pass through one logarithmic unit.

$$z = (T_2 - T_1)/(\log D_1 - \log D_2)$$

where
$T_2 - T_1$ = temperature of treatment in degrees C and
$D_1 - D_2$ = time of decimal reduction in minutes at the corresponding temperatures.

TABLE 1

| Heating temperature (°C.) | D (min) B. licheniformis | B. subtilis | Heating temperature (°C.) |
|---|---|---|---|
| 91 | 120 | 40 | 87 |
| 96 | 22 | 26 | 90 |
| 100 | 6 | 7 | 95 |
| 105 | 3.5 | 6 | 97 |
| z (°C.) | 8.9 | 11.2 | |

Heat resistance in phosphate buffer 0.1 M, pH 7.0 of spores of *Bacillus licheniformis* No. CNCM 1.079 and of *Bacillus subtilis* var. *niger*.

TABLE 2

| Heating temperature (°C.) | B. licheniformis D(min) | Heating temperature (°C.) | B. subtilis D(min) |
|---|---|---|---|
| 40 | 15 | 40 | 39 |
| 45 | 73 | 50 | 18 |
| 50 | 37 | 60 | 5.2 |
| 55 | 20 | 70 | 3 |
| 60 | 12 | 80 | 0.82 |
| 70 | 5 | | |
| | 6.4 | | |
| 80 | 1.6 | | |
| z (°C.) | 21.5 | | 20 |

Destruction of spores of *Bacillus licheniformis* No. CNCM 1.079 by compound A, 0.9%, pH 7.0, and of *Bacillus subtilis* var. *niger* by compound A 2.7%, pH 7.0.

This shows that the effect of compound A compared with heating alone diminishes with increasing temperature.

Linearity of the survival curve

The survival curve is the curve which shows the logarithm of the number of surviving spores as a function of the heating time at a given temperature.

Under ideal conditions the curve is a straight line in the zone of possible measurement ($10^8$ to $10^2$ surviving spores). Under these conditions, the value for D can be calculated exactly and conditions necessary for correct sterilization can be established strictly. It is particularly important to verify that no slowing down of the curve or even formation of a plateau occurs for small numbers of surviving spores (phenomenon known as "trailing") which would indicate the presence of a small proportion of spores which escape treatment. It should be noted that such a verification is virtually never carried out when a new chemical compound having a sporicidal action is discovered.

For this study of compound A, it was necessary not only to make a direct count on the culture medium but also by way of filtration on the membrane in order to prevent any introduction of compound A into the culture medium (growth in a culture medium from heated spores is in fact partly inhibited in the presence of compound A). Under these conditions, the survival curve after heating in the presence of compound A at pH 7.0 was perfectly linear and showed no trailing for the temperatures of 80° and 90° C. The survival curve remained linear at 50° to 70° C. but showed a trail for a destruction level of $10^5$. The survival curve was then no longer linear.

TABLE 3

| Number of surviving spores | | |
|---|---|---|
| Experimental value | Theoretical value | Heating time (min) |
| $4.2.10^8$ | $1.4.10^{9*}$ | 0 |
| $3.3.10^8$ | $3.2.10^8$ | 2 |
| $1.2.10^8$ | $6.0.10^7$ | 4 |
| $1.6.10^7$ | $1.6.10^7$ | 6 |
| $3.1.10^6$ | $3.5.10^6$ | 8 |
| $2.2.10^5$ | $8.2.10^5$ | 10 |
| $8.2.10^4$ | $1.7.10^5$ | 12 |
| $2.4.10^4$ | $1.4.10^4$ | 14 |
| $8.0.10^3$ | $9.0.10^3$ | 16 |
| $1.6.10^3$ | $1.9.10^3$ | 18 |
| $4.5.10^2$ | $4.5.10^2$ | 20 |

Example of a linear survival curve (heating at 50° C. in the presence of compound A, 0.9%, pH 7.0: spores of *B. licheniformis* No. CNCM 1.079)
*The curve had a shoulder of 2 minutes.

TABLE 4

| Number of surviving spores | | |
|---|---|---|
| Experimental value | Theoretical value | Heating time (min) |
| $4.5.10^8$ | $4.5.10^8$ | 0 |
| $9.0.10^7$ | $5.5.10^7$ | 15 |
| $4.5.10^6$ | $6.1.10^6$ | 30 |
| $8.1.10^4$ | $8.8.10^4$ | 60 |
| $7.8.10^3$ | $7.0.10^3$ | 80 |
| $7.0.10^{3*}$ | $3.0.10^1$ | 120 |
| $3.5.10^{4*}$ | <1 | 180 |

Example of a survival curve showing a trail (heating at 60° C. in compound A, 0.9%, pH 7.0); spores of *B. licheniformis* No. CNCM 1.079.
*trail

EXAMPLE 2

Sterilization of the whole sterilization circulation for milk in an apparatus for ultra high temperature treatment of milk is at present carried out at 120° to 130° C. for 30 minutes in moist heat under pressure.

Sterilization with compound A may be carried out as follows: The sterilization parameters are fixed at 80° C. for 20 minutes (or any other treatment which is equivalent from the point of view of its sporicidal action within a temperature range of 80° to 100° C.).

During the first phase, a 1% solution of compound A flows in a closed circuit through the milk sterilization circulation. The temperature of the heating section of the sterilizer is fixed to maintain every point in the circulation at a minimum temperature of 80° C.

After 20 minutes at this temperature, the sterilizer is adjusted to the normal sterilizing conditions and is supplied with water which is thereby sterilized and cooled under the same conditions as will subsequently be applied to the milk. This water serves first to discharge the solution of compound A to a storage vat for later use and then to rinse the apparatus. The transfer from water to milk is then carried out under the same conditions as after sterilization by heat alone.

EXAMPLE 3

Another application of compound A is the decontamination of sections of apparatus which are heavily contaminated with bacterial spores. In the bleaching section of a vegetable sterilization chain, the high temperature prevailing there promotes the growth and sporulation of thermophilic bacterial, capable of multiplying at 65° to 70° C., whose spores are exceptionally resistant. Decontamination of this section, which is not made of a material constructed to be put under pressure and where it is not possible to use the traditional chemical sterilizing agents (acids, bases, chemicals which release chlorine, etc.) because of the risk of corrosion, can be carried out under the same temperature conditions (80° to 100° C.) as above or even at a lower temperature, in the range of 60° to 80° C., since in this case the object is to reduce the contamination by spores to an acceptable level. In view of the resistance of the thermophilic spores, the treatment time should be of the order of 20 to 30 minutes but must be adjusted according to the actual risk of contamination and the frequency with which the decontamination operations are carried out.

We claim:

1. A process for the sterilization or decontamination of apparatus by destruction of spores in contact with said apparatus comprising
    contacting said apparatus for about 1 to about 60 minutes with an aqueous solution containing about 0.5% to about 2% by weight of a heat effective catalyst of the formula

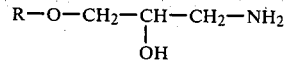

wherein R represents an alkyl radical of from 5 to 14 carbon atoms, or a salt or a base of said compound,
    maintaining the temperature of said solution in the range of about 60° C. to about 100° C., maintaining the pressure of said solution at about atmospheric pressure, and
    correlating the sterilization parameters of time of contact and temperature of solution with respect to the particular strain of spores being treated using moist heat sterilization destruction kinetics data for said strain of spores.

2. Process according to claim 1, wherein said temperature is in the range of 70° to 90° C.

3. Process according to claim 1, wherein said sterilization or decontamination time is from 10 minutes to 30 minutes.

4. Process according to claim 1, wherein said apparatus is maintained in contact with an approximately 1% solution of said compound for a time of about 20 minutes at about 80° C.

5. Process according to claim 1, wherein said solution has a pH the range of about 7 to about 8.

* * * * *